(12) United States Patent
Hares et al.

(10) Patent No.: US 12,150,724 B2
(45) Date of Patent: Nov. 26, 2024

(54) METHODS AND SYSTEMS FOR PROVIDING ASSISTANCE TO A USER OF A SURGICAL ROBOT SYSTEM

(71) Applicant: CMR SURGICAL LIMITED, Cambridge (GB)

(72) Inventors: Luke David Ronald Hares, Cambridge (GB); Paul Christopher Roberts, Cambridge (GB); Rupert Menzies, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 0 days.

(21) Appl. No.: 18/675,489

(22) Filed: May 28, 2024

(65) Prior Publication Data

US 2024/0307136 A1 Sep. 19, 2024

Related U.S. Application Data

(63) Continuation of application No. 17/278,969, filed as application No. PCT/GB2019/052802 on Oct. 3, 2019.

(30) Foreign Application Priority Data

Oct. 3, 2018 (GB) ..................................... 1816166

(51) Int. Cl.
*A61B 34/32* (2016.01)
*A61B 34/00* (2016.01)
(Continued)

(52) U.S. Cl.
CPC .............. *A61B 34/32* (2016.02); *A61B 34/25* (2016.02); *G08B 7/06* (2013.01); *A61B 18/12* (2013.01);
(Continued)

(58) Field of Classification Search
CPC ......... A61B 34/32; A61B 34/25; A61B 18/12; A61B 2034/252; A61B 2034/254; A61B 2034/258; G08B 7/06
See application file for complete search history.

(56) References Cited

U.S. PATENT DOCUMENTS 5,649,021 A 7/1997 Matey et al.
9,901,411 B2 2/2018 Gombert et al.
(Continued)

FOREIGN PATENT DOCUMENTS

CN 102448680 A 5/2012
CN 106102549 A 11/2016
(Continued)

OTHER PUBLICATIONS

United Kingdom Combined Search and Examination Report from corresponding United Kingdom Application No. GB2219756.0 dated Jan. 18, 2023.
(Continued)

*Primary Examiner* — Harry Y Oh
*Assistant Examiner* — Dylan M Katz
(74) *Attorney, Agent, or Firm* — Lando & Anastasi, LLP

(57) ABSTRACT

A system for providing assistance to a user of a surgical robot system, the system comprising: a surgical robot system comprising at least one surgical robot having a base, and an arm extending from the base to an attachment for an instrument, the arm comprising a plurality of joints whereby the configuration of the arm can be altered; and an assistance module comprising a list of steps of a task for which procedural assistance can be provided, the assistance module being configured to: receive, while the surgical robot system is being used to perform the task, status data indicating a status of the surgical robot system; determine, from the status data, whether the surgical robot system is in a
(Continued)

procedural assistance state, the surgical robot system being in a procedural assistance state when the surgical robot system is being, or, is about to be, used to perform one of the steps of the task for which procedural assistance can be provided; and in response to determining that the surgical robot system is in a procedural assistance state, cause the surgical robot system to provide procedural assistance to the user in performing the step of the task while the surgical robot system is being used to perform the task.

12 Claims, 4 Drawing Sheets

(51) Int. Cl.
*G08B 7/06* (2006.01)
*A61B 18/12* (2006.01)

(52) U.S. Cl.
CPC ... *A61B 2034/252* (2016.02); *A61B 2034/254* (2016.02); *A61B 2034/258* (2016.02)

(56) References Cited

U.S. PATENT DOCUMENTS

| | | | |
|---|---|---|---|
| 2009/0192524 A1 | 7/2009 | Itkowitz et al. | |
| 2011/0071473 A1 | 3/2011 | Rogers et al. | |
| 2014/0046128 A1 | 2/2014 | Lee et al. | |
| 2014/0114481 A1 | 4/2014 | Ogawa et al. | |
| 2014/0276951 A1 | 9/2014 | Hourtash et al. | |
| 2016/0279799 A1 | 9/2016 | King et al. | |
| 2016/0331474 A1 | 11/2016 | Lacal et al. | |
| 2018/0092700 A1 | 4/2018 | Itkowitz et al. | |
| 2018/0161108 A1 | 6/2018 | Savall et al. | |
| 2018/0168755 A1 | 6/2018 | Cagle et al. | |
| 2018/0250086 A1 | 9/2018 | Grubbs | |
| 2018/0296096 A1* | 10/2018 | Islam | A61B 5/7445 |
| 2019/0150131 A1 | 5/2019 | Chen et al. | |

FOREIGN PATENT DOCUMENTS

| | | |
|---|---|---|
| EP | 2332477 A2 | 6/2011 |
| EP | 2982330 A1 | 2/2016 |
| EP | 3342560 A1 | 7/2018 |
| EP | 3860496 A1 | 8/2021 |
| GB | 2611255 A | 3/2023 |
| JP | 2014097431 A | 5/2014 |
| JP | 201780887 A | 5/2017 |
| JP | 2017209529 A | 11/2017 |
| WO | 2009158164 A1 | 12/2009 |
| WO | 2014014916 A2 | 1/2014 |
| WO | 2015120008 A1 | 8/2015 |
| WO | 2015142933 A1 | 9/2015 |
| WO | 2015143067 A1 | 9/2015 |
| WO | 2015162256 A1 | 10/2015 |
| WO | 2016069660 A1 | 5/2016 |
| WO | 2017098259 A1 | 6/2017 |
| WO | 2017127202 A1 | 7/2017 |
| WO | 2017146890 A1 | 8/2017 |
| WO | 2018029823 A1 | 2/2018 |
| WO | 2018052796 A1 | 3/2018 |
| WO | 2018089812 A1 | 5/2018 |
| WO | 2020070511 A1 | 4/2020 |

OTHER PUBLICATIONS

Australian Examination Report No. 1 from Standard Patent Application from corresponding Australian Application No. 2022252697 dated Oct. 9, 2023.
Australian Notice of Acceptance for Patent Application from corresponding Australian Application No. 2022252697 dated Jan. 11, 2024.
Chinese Notice of First Office Action from corresponding Chinese Application No. 201980063311.3 dated Dec. 11, 2023.
Indian Examination Report from a corresponding Indian Application No. 202127017273 dated Feb. 25, 2022.
Japanese Decision of Refusal from corresponding Japanese Patent Application No. 2021-517788 dated Dec. 6, 2022.
Japanese Notification of Reasons for Refusal from corresponding Japanese Application No. 2021-517788 dated May 26, 2022.
Notification of Transmittal of the International Search Report and the Written Opinion of the International Searching Authority from corresponding PCT/GB2019/052802 dated Mar. 27, 2020.
United Kingdom Combined Search and Examination Report from corresponding United Kingdom Application No. GB2214754.0 dated Nov. 3, 2022.
United Kingdom Combined Search and Examination Report from corresponding United Kingdom Application No. GB2214755.7 dated Nov. 3, 2022.
United Kingdom Search Report from corresponding United Kingdom Application No. GB1816166.1 dated Mar. 28, 2019.

* cited by examiner

METHODS AND SYSTEMS FOR PROVIDING ASSISTANCE TO A USER OF A SURGICAL ROBOT SYSTEM

CROSS-REFERENCE TO RELATED APPLICATION

This application is a continuation of U.S. patent application Ser. No. 17/278,969, filed Mar. 23, 2021, titled METHODS AND SYSTEMS FOR PROVIDING ASSISTANCE TO A USER OF A SURGICAL ROBOT SYSTEM, which is a U.S. National Phase Application under 35 U.S.C. § 371 of International Application No. PCT/GB2019/052802 [Expired], filed Oct. 3, 2019, which claims the benefit under 35 U.S.C. § 119 of United Kingdom Patent Application No. 1816166.1 filed on Oct. 3, 2018. Each application referenced above is hereby incorporated herein by reference in its entirety for all purposes.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

All surgical procedures, including those performed via surgical robot, are associated with patient risks. Many of the risks can be mitigated by taking certain precautions before, during and after the surgery. However, many of the mitigation techniques that are currently in place are limited by the information that is available before, during and after the surgery. When a surgical robot is used to perform all or a portion of a surgical procedure there is inherently more information available about the procedure. In particular, at a minimum, there is information about the surgical robot-how it interacts with the patient and how the users (e.g. surgical team) interact with it. It would be advantageous to be able to harness that information to be able to improve the efficiency and/or efficacy of surgical procedures performed via surgical robot.

The embodiments described below are provided by way of example only and are not limiting of implementations which solve any or all of the disadvantages of known surgical robot systems.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

Described herein are methods and systems for providing assistance to one or more users of a surgical robot system. The system comprises a surgical robot system and an assistance module. The surgical robot system comprises at least one surgical robot having a base, and an arm extending from the base to an attachment for an instrument, the arm comprising a plurality of joints whereby the configuration of the arm can be altered. The assistance module is configured to receive, while the surgical robot system is being used to perform the task, status data indicating a status of the surgical robot system; determine, from the status data, whether the surgical robot system is in an assistance state; and in response to determining that the surgical robot system is in an assistance state, cause the surgical robot system to provide assistance to one or more of the users while the surgical robot system is being used to perform the task.

A first aspect provides a system for providing assistance to a user of a surgical robot system, the system comprising: a surgical robot system comprising at least one surgical robot having a base, and an arm extending from the base to an attachment for an instrument, the arm comprising a plurality of joints whereby the configuration of the arm can be altered; and an assistance module comprising a list of steps of a task for which procedural assistance can be provided, the assistance module being configured to: receive, while the surgical robot system is being used to perform the task, status data indicating a status of the surgical robot system; determine, from the status data, whether the surgical robot system is in a procedural assistance state, the surgical robot system being in a procedural assistance state when the surgical robot system is being, or, is about to be, used to perform one of the steps of the task for which procedural assistance can be provided; and in response to determining that the surgical robot system is in a procedural assistance state, cause the surgical robot system to provide procedural assistance to the user in performing the step of the task while the surgical robot system is being used to perform the task.

The assistance module may be configured to cause the surgical robot system to provide procedural assistance by causing the surgical robot system to output information that provides guidance on how to perform the step of the task.

The information that provides guidance on how to perform the step of the task may comprise one or more of: information indicating what step or steps are to be performed next, and information indicating which instrument should be attached to the at least one surgical robot next.

The system may further comprise a command interface comprising one or more input devices whereby an operator of the surgical robot system can request motion of an instrument attached to the at least one surgical robot in a desired way; and the information that provides guidance on how to perform the task may comprise information indicating which of the at least one surgical robots is to be associated with each of the one or more input devices.

The information that provides guidance on how to perform the step of the task may comprise information indicating a path that an active surgical robot arm should follow to perform the step of the task in an efficient manner.

The assistance module may be configured to cause the surgical robot system to display on a display screen a recommended path the active surgical robot arm should follow to perform the step of the task.

The assistance module may be configured to dynamically determine the guidance information from status data related to previously performed tasks.

A second aspect provides a system for providing assistance to a user of a surgical robot system, the system comprising: a surgical robot system comprising at least two surgical robots each having a base, and an arm extending from the base to an attachment for an instrument, each arm comprising a plurality of joints whereby the configuration of the arm can be altered, wherein an energised instrument is attached to one of the at least two surgical robot arms and an endoscope is attached to another of the at least two surgical robot arms; and an assistance module configured to: receive, while the surgical robot system is being used to perform a task, status data indicating a status of the surgical robot system; dynamically determine, from the status data, whether the surgical robot system is in an energised instrument hazard state, the surgical robot system being in an energised instrument hazard state when the energised instrument is in motion, when the energised instrument is not in a field of view of the endoscope, and/or when the energised instrument is in a hazard position with respect to a patient and/or another instrument; and in response to determining that the surgical robot system is in an energised instrument hazard state, cause the surgical robot system to provide energised instrument hazard assistance to the user while the surgical robot system is being used to perform the task.

The energised instrument may be an electrosurgical instrument, or an electrocautery instrument, which is energised by an electrical current to perform a surgical function.

The status data may comprise information on a status of the energised instrument.

The information on the status of the energised instrument may comprise information on whether or not the energised instrument is currently energised.

The assistance module may be configured to cause the surgical robot system to provide energised instrument hazard assistance by causing the surgical robot system to prevent energisation of the energised instrument.

The assistance module may be configured to cause the surgical robot system to prevent energisation of the energised instrument by sending a control signal to a control unit of the surgical robot system which causes the control unit to prevent an energising electrical current from being sent to the energised instrument.

The assistance module may further be configured to request user input on whether the energisation prevention is to be overridden; and in response to receiving user input that the energisation prevention is to be overridden, cause the surgical robot system to allow energisation of the energised instrument.

The assistance module may be configured to cause the surgical robot system to provide energised instrument hazard assistance by causing the surgical robot system to output assistance information, the assistance information notifying one or more users of the surgical robot system that the energised instrument hazard state has been detected and/or that the energised instrument cannot be energised.

Outputting the assistance information to the user may comprise displaying at least at portion of the assistance information on a display of the surgical robot system.

Outputting assistance information to the user may comprise audibly conveying at least a portion of the assistance information to the user.

The assistance module may further be configured to determine, from the status data, whether the surgical robot system is in a hazard state; and in response to determining that the surgical robot system is in a hazard state cause the surgical robot system to provide hazard assistance to the user while the surgical robot system is being used to perform the task.

The assistance module may be configured to determine that the surgical robot system is in a hazard state when the assistance module determines, from the status data, that the surgical robot system is in at least one of a collision state, a faulty instrument state, and an incorrect instrument state.

The surgical robot system may comprise at least two surgical robots each attached to an instrument and the assistance module may be configured to determine that the surgical robot system is in a collision state when the assistance module determines, from the status data, that at least two surgical robot arms have collided or are about to collide, at least two instruments have collided or are about to collide, or an instrument and a surgical robot arm have collided or are about to collide.

The assistance module may be configured to determine that the surgical robot system is in an incorrect instrument state when the assistance module determines, from the status data, that an instrument has been attached to a surgical robot arm that is not suitable for the task or a current step of the task.

The assistance module may be configured to, in response to determining that the surgical robot system is in an incorrect instrument state cause the surgical robot system to automatically perform an instrument change so that the instrument that is not suitable for the task or a current step of the task is replaced with an instrument suitable for the task of the current step of the task.

The assistance module may further be configured to determine, from the status data, whether the surgical robot system is in a predicted hazard state, the surgical robot system being in a predicted hazard state when one or more hazard indicators are detected from the status data; and in response to determining that the surgical robot system is in a predicted hazard state cause the surgical robot system to provide predicted hazard assistance to the user while the surgical robot system is being used to perform the task.

The one or more hazard indicators may comprise events or patterns in the status data of previously performed tasks that preceded a hazard.

The task may be a surgical procedure performed on a patient and at least one of the one or more hazard indicators may comprise one or more of: one or more vital signs and/or one or more other health metrics of the patient falling outside a predetermined range; one or more vital signs and/or one or more other health metrics of an operator of the surgical robot system falling outside a predetermined range; one or more individuals present for the task speaking in a raised voice; and one or more individuals present for the task speaking a warning word or phrase.

The assistance module may further be configured to determine, from the status data, whether the surgical robot system is in a skill assistance state, the surgical robot system being in a skill assistance state when the surgical robot system is currently being, or, is about to be, used to perform a known skill; and in response to determining that the surgical robot system is in a skill assistance state, the assistance module is configured to control one or more surgical robot arms to automatically perform the known skill.

A level of assistance provided may be based on a skill level of an operator of the surgical robot system.

The assistance module may be configured to dynamically determine the operator's skill level based on the status data.

A third aspect provides a computer-implemented method of providing assistance to a user of a surgical robot system, the method comprising: receiving, while a surgical robot system is being used to perform a task comprising a plurality of steps, status data indicating a status of the surgical robot system, the surgical robot system comprising at least one surgical robot having a base, and an arm extending from the base to an attachment for an instrument, the arm comprising a plurality of joints whereby the configuration of the arm can be altered; determining, from the status data, whether the surgical robot system is in a procedural assistance state, the surgical robot system being in a procedural assistance state when the surgical robot system is being, or, is about to be, used to perform one of the steps of the task for which procedural assistance can be provided; and in response to determining that the surgical robot system is in a procedural assistance state, causing the surgical robot system to provide procedural assistance to the user in performing the step of the task while the surgical robot system is being used to perform the task.

A fourth aspect provides a computer-implemented method of providing assistance to a user of a surgical robot system, the method comprising: receiving, while a surgical robot system is being used to perform a task, status data indicating a status of the surgical robot system, the surgical robot system comprising at least two surgical robots each having a base, and an arm extending from the base to an attachment for an instrument, each arm comprising a plurality of joints whereby the configuration of the arm can be altered, wherein an energised instrument is attached to one of the at least two surgical robot arms and an endoscope is attached to another of the at least two surgical robot arms; dynamically determining, from the status data, whether the surgical robot system is in an energised instrument hazard state, the surgical robot system being in an energised instrument hazard state when the energised instrument is in motion, when the energised instrument is not in a field of view of the endoscope, and/or when the energised instrument is in a hazard position with respect to a patient and/or another instrument; and in response to determining that the surgical robot system is in an energised instrument hazard state, causing the surgical robot system to provide energised instrument hazard assistance to the user while the surgical robot system is being used to perform the task.

A fifth aspect provides a system for providing assistance to a user of a surgical robot system, the system comprising: a surgical robot system comprising at least one surgical robot having a base, and an arm extending from the base to an attachment for an instrument, the arm comprising a plurality of joints whereby the configuration of the arm can be altered; and an assistance module configured to: receive, while the surgical robot system is being used to perform a task, status data indicating a status of the surgical robot system; determine, from the status data, whether the surgical robot system is in an assistance state; and in response to determining that the surgical robot system is in an assistance state, cause the surgical robot system to provide assistance to the user while the surgical robot system is being used to perform the task.

The assistance module may be configured to determine whether the surgical robot system is in an assistance state by comparing the status data to status data for previously performed tasks.

The assistance module may be configured to cause the surgical robot system to provide assistance by controlling movement of a surgical robot arm.

The assistance module may be configured to control the movement of a surgical robot arm by causing the surgical robot arm to move so as to automatically perform at least a portion of the task.

The assistance module may be configured to control the movement of the surgical robot arm by inhibiting the movement of the surgical robot arm.

The assistance module may be configured to only control the movement of the surgical robot arm in response to receiving input from the user confirming that the surgical robot arm can be automatically controlled.

The assistance module may be configured to cause the surgical robot system to provide assistance by causing the surgical robot system to output assistance information to the user.

Outputting the assistance information to the user may comprise displaying at least at portion of the assistance information on a display of the surgical robot system.

Outputting assistance information to the user comprises audibly conveying at least a portion of the assistance information to the user.

The assistance module may be configured to determine that the surgical robot system is in an assistance state when the assistance module determines, from the status data, that the surgical robot system is in a hazard state.

The assistance module may be configured to determine that the surgical robot system is in a hazard state when the assistance module determines, from the status data, that the surgical robot system is in at least one of a collision state, a faulty instrument state, an incorrect instrument state, an energised instrument hazard state, and a potential hazard state.

The surgical robot system may comprise at least two surgical robots and the assistance module may be configured to determine that the surgical robot system is in a collision state when the assistance module determines, from the status data, that at least two surgical robot arms have collided or are about to collide, at least two instruments have collided or are about to collide, or an instrument and a surgical robot arm have collided or are about to collide.

The assistance module may be configured to determine that the surgical robot system is in an incorrect instrument state when the assistance module determines, from the status data, that an instrument has been attached to a surgical robot arm that is not suitable for the task or a current step of the task.

The assistance module may be configured to, in response to determining that the surgical robot system is in an incorrect instrument state cause the surgical robot system to automatically perform an instrument change so that the incorrect instrument is replaced with a suitable instrument.

The surgical robot system may comprise at least two surgical robots; an energised instrument may be attached to one of the surgical robot arms and an endoscope is attached to another of the surgical robot arms; and the assistance module may be configured to determine that the surgical robot system is in an energised instrument hazard state when the assistance module determines, from the status data, that the energised instrument is in motion, that the energised instrument is not in the field of view of the endoscope, and/or that the energised instrument is in a hazard position with respect to a patient and/or another instrument.

The assistance module may be configured to determine that the surgical robot system is in an assistance state when the assistance module determines, from the status data, that the surgical robot system is in a predicted hazard state, the surgical robot system being in a predicted hazard state when one or more hazard indicators are detected from the status data.

The one or more hazard indicators may comprise events or patterns in the status data of previously performed tasks that preceded a hazard.

The task may be a surgical procedure on a patient and at least one of the one or more hazard indicators may comprise one or more of: one or more of the patient's vital signs and/or other health metrics falling outside a predetermined range; one or more of an operator's vital signs and/or other health metrics falling outside a predetermined range; one or more of the individuals present for the task speaking in a raised voice; and one or more of the individuals present for the task speaking a warning word or phrase.

The assistance module may be configured to determine that the surgical robot system is in an assistance state when the assistance module determines, from the status data, that the surgical robot system is in a skill assistance state, the surgical robot system being in a skill assistance state when the surgical robot is currently being, or, is about to be, used to perform a known skill; and in response to determining that the surgical robot system is in a skill assistance state, the assistance module is configured to control one or more surgical robot arms to automatically perform the known skill.

A level of assistance provided may be based on a skill level of an operator of the surgical robot system.

The assistance module may be configured to dynamically determine the operator's skill level based on the status data.

The task may be a surgical procedure.

A sixth aspect provides a computer-implemented method of providing assistance to a user of a surgical robot system, the method comprising: receiving, while a surgical robot system is being used to perform a task, status data indicating a status of the surgical robot system, the surgical robot system comprising at least one surgical robot having a base, and an arm extending from the base to an attachment for an instrument, the arm comprising a plurality of joints whereby the configuration of the arm can be altered; determining, from the status data, whether the surgical robot system is in an assistance state; and in response to determining that the surgical robot system is in an assistance state, causing the surgical robot system to provide assistance to the user while the surgical robot system is being used to perform the task.

The above features may be combined as appropriate, as would be apparent to a skilled person, and may be combined with any of the aspects of the examples described herein.

BRIEF DESCRIPTION OF THE DRAWINGS

Examples will now be described in detail with reference to the accompanying drawings in which.

Figure 1:
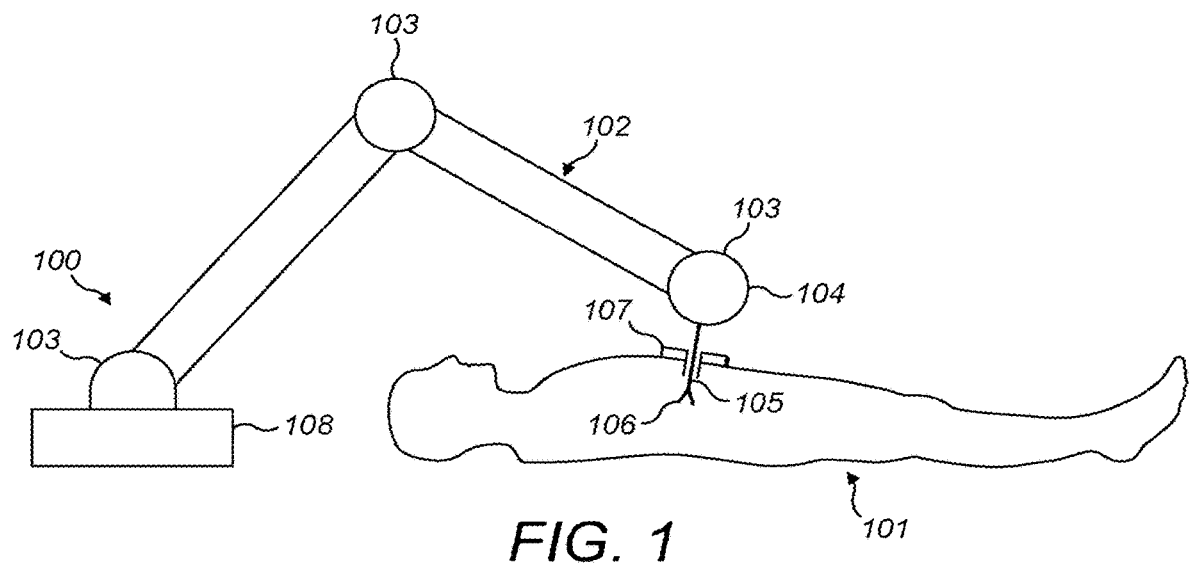
FIG. 1 is a schematic diagram of an example surgical robot performing a surgical procedure.

The accompanying drawings illustrate various examples. The skilled person will appreciate that the illustrated element boundaries (e.g., boxes, groups of boxes, or other shapes) in the drawings represent one example of the boundaries. It may be that in some examples, one element may be designed as multiple elements or that multiple elements may be designed as one element. Common reference numerals are used throughout the figures, where appropriate, to indicate similar features.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

Described herein are methods and systems for dynamically providing assistance to one or more users of a surgical robot system while the surgical robot system is being used to perform a task. The systems comprise a surgical robot system that comprises one or more surgical robots; and an assistance module in communication with the surgical robot system. The assistance module is configured to: receive, while the surgical robot system is being used to perform the task, status data indicating a status of the surgical robot system; determine, from the status data, whether the surgical robot system is in an assistance state; and in response to determining that the surgical robot system is in an assistance state, cause the surgical robot system to provide assistance to one or more of the users of the surgical robot system while the surgical robot is being used to perform the task. The users of the surgical robot system include the operator (e.g. surgeon) controlling the surgical robot system and/or the other individuals that are part of a team (e.g. surgical or operating room team) that is present for, and participates in, the task (e.g. surgery).

Figure 3:
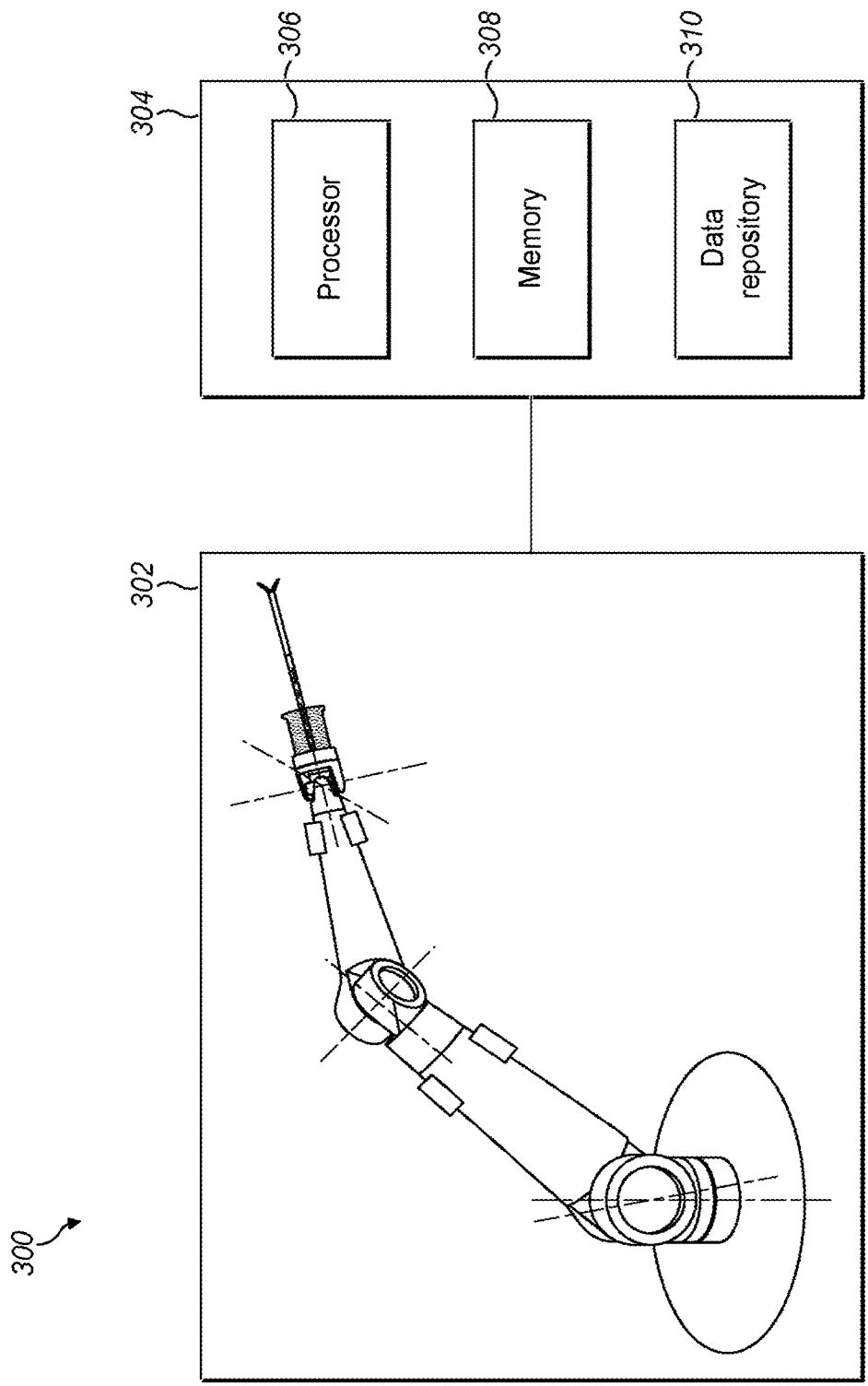
FIG. 3 is a block diagram of an example system for providing assistance to one or more users of a surgical robot system.

Reference is first made to FIG. 3 which illustrates an example system 300 for providing assistance to one or more users of a surgical robot system. The system 300 comprises a surgical robot system 302; and an assistance module 304 in communication with the surgical robot system 302. The surgical robot system 302 comprises at least one surgical robot having a base, and an arm extending from the base to an attachment for a surgical instrument, the arm comprising a plurality of joints whereby the configuration of the arm can be altered. An example surgical robot system 302 is described below with reference to FIG. 4.

The assistance module 304 is configured to receive status data that indicates the status of the surgical robot system 302. As described in more detail below, the status data may comprise any information about the surgical robot system 302 or about the environment in which the surgical robot system 302 is operating. The assistance module 304 may receive status data from the surgical robot system itself (e.g. data relating to the position and or movement of the surgical robot arm(s)) and/or from an external source. The assistance module 304 may receive the status data from the surgical robot system 302 and/or from an external source via any suitable means. For example, the assistance module 304 may receive status data from the surgical robot system 302 and/or from an external source via a wireless or wired communication connection such as not limited to, an Ethernet connection, Wi-Fi® connection, Bluetooth® connection, Near-Field Communication (NFC) connection or the like. At least a portion of the status data is provided to the assistance module 304 in real time (or in substantially real time) while the surgical robot system is being used to perform a task (e.g. surgery).

The assistance module 304 is configured to analyse the status data to determine whether the surgical robot system is in an assistance state (i.e. a state in which assistance can be provided to one or more users of the surgical robot system). As described in more detail below, the assistance module 304 may determine that the surgical robot system is an assistance state by identifying certain events or patterns in the status data and/or by comparing the status data to status data of previously performed tasks. For example, the assistance module 304 may be configured to determine that the surgical robot system is in an assistance state if the assistance module 304 determines that a collision is about to occur or has occurred between arms of the surgical robot system.

If the assistance module 304 determines that the surgical robot system 302 is in an assistance state, the assistance module 304 causes the surgical robot system to dynamically provide assistance to one or more users of the surgical robot system in performing the task. As described in more detail below, causing the surgical robot system to provide assistance to one or more users of the surgical robot may comprise controlling all or a portion of the movement of one or more of the surgical robot arms and/or or causing the surgical robot system to provide assistance information to a user (e.g. audibly or via a display). The type and form of the assistance that is provided to the user(s) may be based on the particular assistance state that the surgical robot system 302 is in. For example, if the assistance module 304 determines that a collision is about to occur, or has occurred, between arms of the surgical robot system, the assistance module 304 may be configured to cause the surgical robot system to inhibit movement of the robot arms. In some cases, prior to causing the surgical robot system 302 to provide assistance to a user of the surgical robot system in performing the task, the assistance module 304 may be configured to request input from the user(s) as to whether they wish assistance to be provided. In these cases, the assistance module 302 may be configured to only cause the surgical robot system 302 to provide assistance to a user of the surgical robot system in response to receiving input indicating that assistance is to be provided. An example method that may be executed by the assistance module 304 to provide assistance to one or more users of the surgical robot system in performing a task is described below with reference to FIG. 5.

The assistance module 304 may comprise a processor 306 and a memory 308. The memory 308 stores in a non-transient way software that is executable by the processor 306 to receive status data, determine from the status data whether the surgical robot system 302 is in an assistance state, and if an assistance state is detected cause the surgical robot system to provide assistance to one or more users of the surgical robot system. In some cases, the assistance module 304 may also comprise a data repository 310 which is used to store status data for previously performed tasks. As described above, in some cases the assistance module 304 may be configured to identify that the surgical robot system is in an assistance state by comparing the received status data to status data of previously performed tasks.

Figure 4:
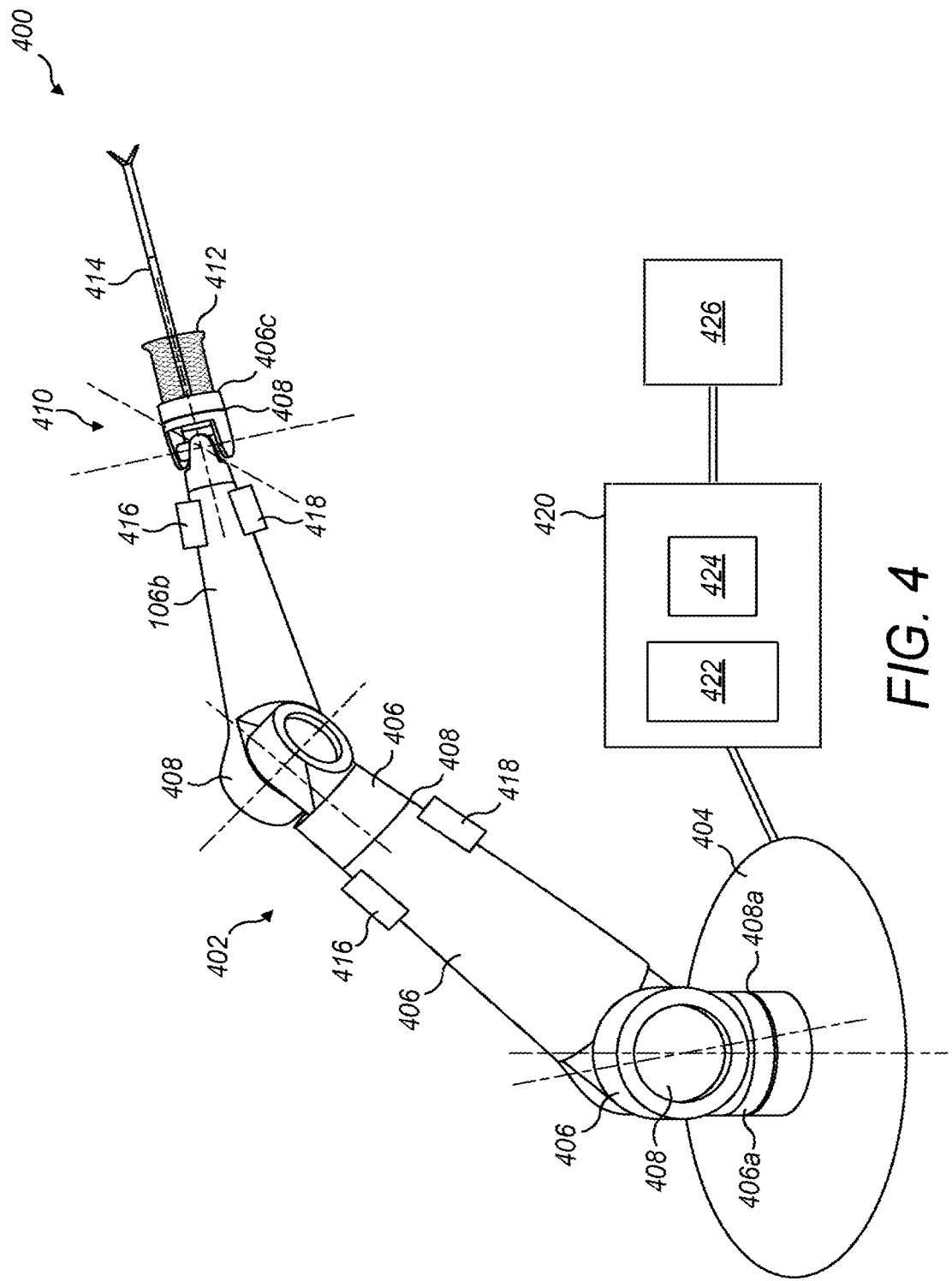
FIG. 4 is a schematic diagram of an example surgical robot system.

Reference is now made to FIG. 4 which illustrates an example surgical robot system 400. The surgical robot system 400 of FIG. 4 comprises a surgical robot having an arm 402 which extends from a base 404. The arm 402 comprises a number of rigid limbs 406. The limbs are coupled by revolute joints 408. The most proximal limb 406a is coupled to the base 404 by joint 408a. It and the other limbs are coupled in series by further ones of the joints 408. In some cases, the wrist 410 may be made up of four individual revolute joints. The wrist 410 couples one limb (406b) to the most distal limb (406c) of the arm 402. The most distal limb 406c carries an attachment 412 for an instrument 414. Each joint 408 of the arm 402 has one or more motors 416 which can be operated to cause rotational motion at the respective joint, and one or more position and/or torque sensors 418 which provide information regarding the current configuration and/or load at that joint. Suitably, the motors 416 are arranged proximally of the joints whose motion they drive, so as to improve weight distribution. For clarity, only some of the motors and sensors are shown in FIG. 4. The arm may be generally as described in our co-pending patent application PCT/GB2014/053523.

Figure 2:
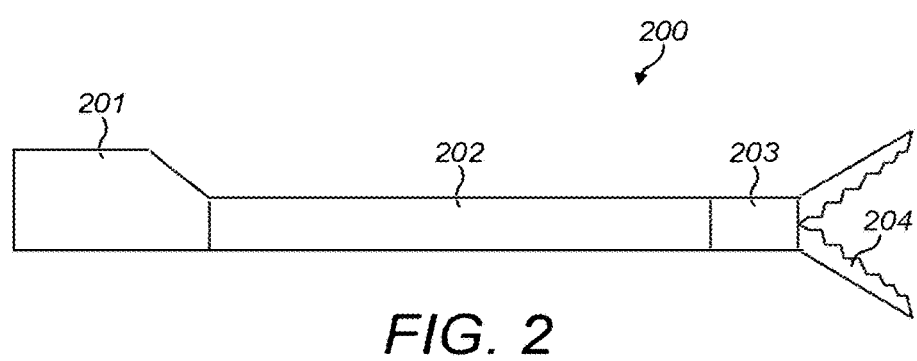
FIG. 2 is a schematic diagram of an example surgical instrument.

The arm terminates in an attachment 412 for interfacing with the instrument 414. The instrument 414 may take the form as described with respect to FIG. 2. The instrument may have a diameter less than 8 mm. In some cases, the instrument may have a 5 mm diameter. In other cases, the instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 412 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation. Features of the drive assembly interface and the instrument interface aid their alignment when brought into engagement with each other, so as to reduce the accuracy with which they need to be aligned by the operator (e.g. surgeon).

The instrument 414 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 420. The control unit 420 comprises a processor 422 and a memory 424. The memory 424 stores in a non-transient way software that is executable by the processor 422 to control the operation of the motors 416 to cause the arm 402 to operate in the manner described herein. In particular, the software can control the processor 422 to cause the motors (for example via distributed controllers) to drive in dependence on inputs from the sensors 418 and from an operator (e.g. surgeon) command interface 426. The control unit 420 is coupled to the motors 416 for driving them in accordance with outputs generated by execution of the software. The control unit 420 is coupled to the sensors 418 for receiving sensed input from the sensors, and to the command interface 426 for receiving input from it. The respective couplings may, for example, each be electrical or optical cables, or may be provided by a wireless connection. The command interface 426 comprises one or more input devices whereby an operator (e.g. surgeon) can request motion of the end effector in a desired way. The input devices could, for example, be manually operable mechanical input devices such as control handles or joysticks, or contactless input devices such as optical gesture sensors. The software stored in memory 424 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, an operator (e.g. surgeon) at the command interface 426 can control the instrument 414 to move in such a way as to perform a desired surgical procedure. The control unit 420 and/or the command interface 426 may be remote from the arm 402.

Although the example surgical robot system 400 of FIG. 4 comprises a single surgical robot with a single robot arm, other surgical robot systems may comprise a plurality of surgical robots and/or a plurality of robot arms. For example, other example surgical robot systems may comprise a surgical robot with a plurality of robot arms that can each receive and manipulate a surgical instrument; or they may comprise a plurality of surgical robots that each have a robot arm that can receive and manipulate a surgical instrument.

Figure 5:
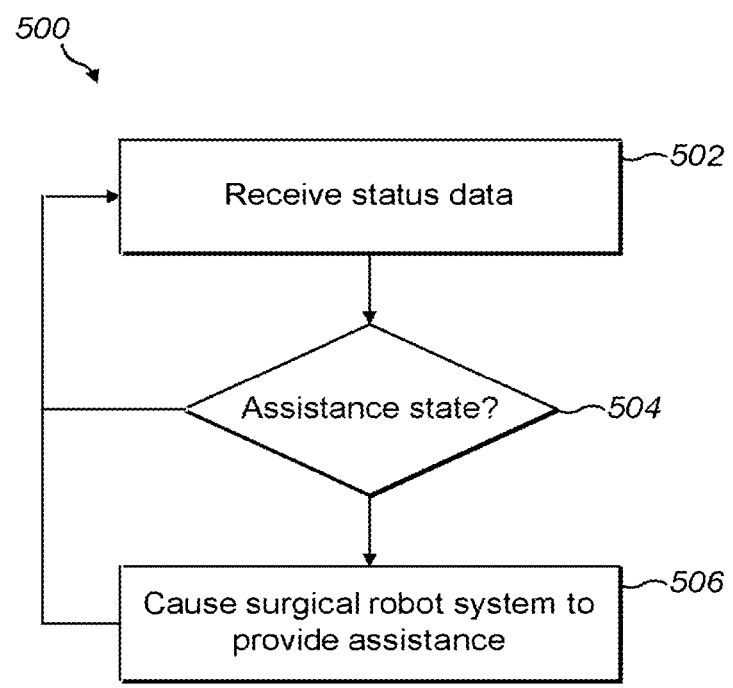
FIG. 5 is a flow diagram of an example method of providing assistance to one or more users of a surgical robot system.

Reference is now made to FIG. 5 which illustrates an example method 500 which may be implemented by the assistance module 304 of FIG. 3 to provide assistance to one or more users of a surgical robot system while the surgical robot system is being used to perform a task (e.g. to perform surgery). The method 500 begins at block 502 where the assistance module 304 receives status data that indicates the status of the surgical robot system 302. The status data may comprise any information about the surgical robot system 302 or about the environment in which the surgical robot system 302 is operating. At least a portion of the status data is received in real time (or in substantially real time) while the surgical robot system is being used to perform a task.

For example, the status data may comprise information or data that describes the current state of the robot arm(s) such as, but not limited to, position and/or torque information that indicates the position and/or movement of the robot arm(s), or the joints thereof. In particular, the status data may comprise the position and/or torque data generated by the position and/or torque sensors 418. It will be evident to a person of skill in the art that this is an example only and that the surgical robot(s) may comprise other sensors that provide information on the status of the robot arm(s).

The status data may also, or alternatively, comprise data or information that describes the state of the instruments attached to the robot arm(s). For example, the status data may comprise information identifying whether there is an instrument attached to the robot arm(s) and, if so, the type of instrument attached to the robot arm(s). In particular, the surgical robot system may comprise means for detecting whether an instrument is attached to the arm (e.g. the surgical robot system may comprise an instrument engagement means such as that described in the Applicant's published patent application GB 2552855 A which is herein incorporated by reference), and means for automatically detecting the type of instrument (e.g. each instrument may comprise an RFID or other component which is configured to automatically provide information on its identity to the surgical robot system when it is attached to a robot arm) and this information may be provided to the assistance module 304 as status data. The status data may also, or alternatively, comprise information such as, but not limited to, position and/or torque information that indicates the position and/or movement of the instrument(s) attached to the robot arm(s). It will be evident to a person of skill in the art that this is an example only and that that the surgical robot or the instruments themselves may comprise other sensors that provide information of the status of the instruments.

Where at least one of the instruments attached to the robot arm(s) is an energised instrument such as, but not limited to, an electrocautery instrument or an electrosurgical instrument, which is energised by an electrical current to perform a surgical function (e.g. cauterising, cutting etc.), the status data may comprise information on the status of the energised instruments such as, but not limited to, whether or not the energised instrument is currently being energised, and if so, the waveform of the electrical current that is used to energise the instrument.

Where at least one of the instruments attached to the robot arm(s) is an endoscope which is inserted to the body and captures images (e.g. a video) of the interior of the patient's body, the status data may comprise the images (e.g. video) captured by the endoscope. As described in Applicant's co-pending UK patent application entitled AUTOMATIC ENDOSCOPE VIDEO AUGMENTATION and filed the same day as the present application which is herein incorporated by reference, in some cases when the surgical robot system is being used to perform a task (e.g. surgical procedure) and an event is detected during the task the images (e.g. video) captured by the endoscope may be automatically augmented with information identifying the detected event. The status data may also, or alternatively comprise information indicating the position, movement, and/or field of view of the endoscope.

The status data may also, or alternatively, comprise data that describes the state of the operator input devices which are used to control the operation of the robot arms and instruments. As described above, the operator input devices could, for example, be manually operable mechanical input devices such as control handles or joysticks. In these cases, the status data may comprise data such as, but not limited to, position and/or torque data that indicates the position and/or movement of the input devices.

The status data may also, or alternatively comprise, information on the mode of operation of the surgical robot system 302. For example, in some cases the surgical robot system may be able to operate in one of a plurality modes such as, but not limited to, an active mode in which the operator (e.g. surgeon) is controlling one or more of the robot arms to perform a task; a selection mode in which the operator (e.g. surgeon) is selecting or switching which robot arm(s) they are going to control from the command interface; and an instrument change mode in which at least one of the instruments attached to a robot arm is being removed, attached and/or changed. There may also be several types of active mode. For example, in some cases there may be an endoscope active mode in which the operator is controlling an endoscope attached to a robot arm and an instrument active mode in which the operator is controlling one or more other instruments attached to a robot arm. In these cases, the status data may comprise information on the current operating mode of the surgical robot system. It will be evident to a person of skill in the art that these are example modes of operation of a surgical robot system and that there may be additional or different modes of operation of the surgical robot system.

Where the task being performed is a surgical procedure performed on a patient, the status data may also, or alternatively, comprise data related to the patient. For example, the status data may comprise patient health information or data that describes the status of the patient's health. For example, the status data may comprise information on the patient's vital signs (e.g. body temperature, pulse rate, respiration rate) or other health metrics (e.g. blood pressure, oxygen saturation, blood glucose/sugar). Typically, during surgery, the patient's vital signs and other health metrics are measured by special medical measurement equipment, such as, a heart rate monitor, a pulse oximeter, a continuous glucose monitor (CGM) device and the like. In these cases, the medical measurement equipment may be configured to send the vital sign information or other patient metric information to the assistance module via, for example, a communication network (e.g. a wired or wireless communication network). However, in other cases, information on the patient's vital signs and/or other patient health metrics may be obtained in another manner. For example, in some cases the operating room in which the surgical procedure is being performed may be equipped with a video and/or audio recording device and the vital sign data and/or other patient metric data may be obtained from the video and/or audio recording. For example, where the medical measurement equipment produces an audible representation of the measurement (e.g. a set of audible tones or "beeps") an estimate of the measurement may be obtained through analysis of the audio recorded by the video and/or audio recording device. The status data may also, or alternatively, comprise other information related to the patient, such as, but not limited to demographic information such as age and weight, and other medical information such as previous scans (e.g. x-rays, MRIs), previous outcomes, medical history, diagnosis history and/or treatment plan.

In some cases, the status data may also comprise surgeon health information or data that describes the health of the surgeon controlling the surgical robot system. For example, the status data may comprise information or data on one or more vital signals (e.g. body temperature, pulse rate, respiration rate) and/or other health metrics (e.g. blood pressure) of the surgeon. For example, in some cases, where the input devices are hand-held controllers the hand-held controllers may comprise sensors that measure the heart rate of the surgeon, the shakiness of the surgeon's movement, and/or the sweat rate of the surgeon and provide information or data related to the measured heart rate, shakiness and/or sweat rate to the assistance module 304. In other cases, there may be external medical devices, or the like, that are configured to measure the vital signs or other health metrics of the surgeon. As described above with respect to the patient vital signs and other health metrics, the medical devices that measure the surgeon's vital signs or other health metrics may be configured to provide data on the measured metrics to the assistance module 304 via, for example, a communication network, or an estimate of the measured metrics may be obtained through other means (e.g. by analysis of video and/or audio of the operating room).

As described above, in some cases the room (e.g. operating room) in which the task is being performed may be equipped with audio and/or video recording equipment to record the sound in the room and/or a visual image of the room while the task is being performed. In these cases, the status data may also, or alternatively, comprise the video and audio data captured by the audio and/or video recording equipment.

In some cases, the status data, may also, or alternatively, comprise information on the task being performed. For example, the status data may comprise information on the task (e.g. surgical procedure) being performed by the surgical robot system. In some cases, where the task comprises a number of steps, the status information may comprise information indicating the step of the task that is currently being performed by the surgical robot system. For example, the operator (e.g. surgeon) of the surgical robot system may be able to indicate which step of the task he/she is currently performing, and this information may be provided to the assistance module 304 as status data.

In some cases, the status data may also, or alternatively, comprise information on the users of the surgical robot system (e.g. the operator (e.g. surgeon) controlling the surgical robot(s) and/or other members of the task team (e.g. surgical team)). For example, in some cases, before the task is started, information may be provided to the surgical robot system and/or the assistance module which indicates the users that will be performing the task. In other cases, the users (e.g. surgical team) performing the task (e.g. surgery) may be equipped with a device (e.g. RFID device, mobile telephone, tablet etc.) that may automatically transmit information to the surgical robot system and/or the assistance module 304 that identifies the user when they are in the vicinity of the surgical robot system. An example of such a system is described in the Applicant's co-pending UK patent application entitled "DEVICE INTEROPERATION" and filed the same day as the current application which is herein incorporated by reference.

Once the status data has been received by the assistance module 304 the method 500 proceeds to block 504. In some cases, the assistance module 304 may be configured to collect status data for a predetermined amount of time before proceeding to block 504. The predetermined period of time may be short (e.g. less than 50 ms) so that the assistance module 304 can react quickly to detected assistance states. In other cases, the assistance module 304 may only have a fixed amount of memory to store the status data and may be configured to collect status data until the memory for storing the status data is full.

At block 504, the assistance module 304 determines, based on the status data, whether the surgical robot system 302 is in an assistance state. The term "assistance state" is used herein to mean that the surgical robot system is in a state in which assistance can be provided to one or more users of the surgical robot system via the surgical robot system. Assistance states include, but are not limited to, hazard states in which a hazard or potential hazard has been detected and assistance can be provided to avoid or minimize the hazard; and aid states in which a hazard or a potential hazard has not been detected but assistance can be provided to one or more users in performing the task (e.g. surgery).

Examples of hazard states include, but are not limited to, a collision state in which there has been (or is about to be) a collision between multiple robot arms, multiple instruments, or a robot arm and an instrument; an incorrect end instrument state in which an incorrect instrument for the current task or step of the task is attached to a robot arm; a faulty instrument state in which one of the instruments attached to a robot arm is faulty or needs to be replaced; an energised instrument hazard state in which a hazard related to an energised instrument has been detected; and a potential hazard state in which a hazard is predicted based on, for example, events or patterns detected from the status data.

Examples of aid states include, but are not limited to, skill assistance states in which the surgical robot system is being used to perform a particular skill in which assistance can be provided to perform the skill; and procedure assistance states in which the surgical robot system can provide procedural assistance in performing the task or a portion of the task and/or preparing for the task or a portion of the task. The term "skill" is used herein to mean a distinct activity which the surgical robot system can be used to perform, such as, but not limited to, suturing or a knot. A skill may be performed one or more times during a task (e.g. surgical procedure).

The assistance module 304 may be configured to determine whether the surgical robot system 302 is in an assistance state based on the status data independently (e.g. by detecting events or patterns from the status data) and/or based on a comparison of the status data with status data for previously performed tasks. For example, as described above, in some cases the assistance module 304 may comprise, or have access to, a data repository 310 of status data for previously performed tasks. The previously performed tasks may have been performed by the same surgical robot system and/or another surgical robot system. The previously performed tasks may have been performed by the same operator (e.g. surgeon) and/or other operators (e.g. surgeons). The previously performed tasks may include the same type of task (e.g. same type of surgical procedure) relative to the task currently being performed and/or other types of task (e.g. different types of surgical procedure or a different surgical procedure).

As described above, in some cases the status data may comprise data or information indicating the position and/or motion of the robot arm(s) and/or the instruments attached thereto. In these cases, the assistance module 304 may, for example, be configured to detect that the surgical robot system is in a collision state (i.e. that a robot arm or instrument is about to collide, or has already collided, with another robot arm or instrument) based on the data or information indicating the position and/or motion of the robot arms and/or instruments. For example, the assistance module 304 may be configured to estimate the trajectory of the robot arms and/or instruments based on the position and/or motion data for the robot arms and/or instruments and estimate that there is going to be a collision based on the estimated trajectories. The assistance module 304 may also, or alternatively, be configured to determine that a collision has already occurred between arms, between instruments, or between an arm and an instrument by, for example, (i) determining or estimating the position of the arms and/or instruments from the position and/or motion data and determining that the positions of one or more instruments and/or one or more arms are the same or are substantially similar; or (ii) determining from the position and/or motion information (e.g. torque data) that equal and opposite forces have been detected on two of the arms and/or instruments as described in the Applicant's UK Patent Application No. 1810754.0 which is herein incorporated by reference.

The assistance module 304 may, for example, be configured to detect that the surgical robot system 302 is in an incorrect instrument state when the assistance module 304 detects from the status data that an instrument of a particular type has been attached to an arm and an instrument of that particular type is not suitable for the task being performed or is not suitable for the particular step of the task currently being performed. As described above, in some cases the status data may comprise information indicating the type of instruments currently attached to the robot arms. In these cases, the assistance module 304 may be configured to detect that the surgical robot system 304 is in an incorrect instrument state by comparing the types of instruments currently attached to a robot arm against a list of instruments suitable for performing the current task, or the current step of the task. In some cases, the list of instruments suitable for performing a particular task or a step of a task may be predetermined and loaded into the assistance module 304 prior to the start of the task. In other cases, the assistance module 304 may be configured to dynamically generate a list of instruments suitable for performing the task or the step of the task based on the status data for previously performed tasks. For example, the assistance module 304 may be configured to determine from the status data for previously performed tasks a set of instruments that have been used for a particular task or a particular step of a task.

As described above, in some cases the status data may comprise information identifying the task being performed and, optionally the step of the task being performed. In these cases, the assistance module 304 may be able to identify the current task and, optionally the current step of the task directly from the task/step identifying information. Where information explicitly identifying the task, and/or the step of the task, currently being performed is not received as part of the status data the assistance module 304 may be configured to dynamically detect the task and/or the current step of the task from the other status data. For example, the assistance module 304 may be configured to detect the task and/or the step of the task based on patterns detected in the status data that match patterns in the status data for previously performed tasks. In particular, the assistance module 304, or another computing-based device, may be configured to analyse the status data related to previously performed tasks of the same type as the current task (e.g. status data related to the same surgical procedure or the same type of surgical procedure); identify a common set of steps in that task based on the analysis; and generate a map that links the identified steps. In some cases, the steps of a task (and thus a current step of a task) may be identified based on one or more of the combination of instruments used, and/or the movements of the instruments and/or robot arms.

The assistance module 304 may be configured to detect that the surgical robot system 302 is in a faulty instrument state if the assistance module 304 detects, for example, that an instrument attached to a robot arm has been used a predetermined number of times. Specifically, many surgical instruments can only safely be used a predetermined number of times before they should be replaced. The number of times that a surgical instrument can be used before having to be replaced may vary between instrument type and/or instrument manufacturer. As described above, in some cases the status data may comprise information identifying the instruments attached to the arm(s). For example, each instrument may be identified by a unique identifier. In these cases, the assistance module 304 may maintain, or have access to, a listing of each instrument that could be used in performing the task (e.g. each instrument owned by the hospital in which the surgical procedure is being performed) that indicates how many times that instrument has been used. When the assistance module 304 detects (via the instrument identifier) that a particular instrument has been used in the current task it updates the listing to reflect that the instrument has been used an additional time. If the assistance module 304 detects that the number of uses of a particular instrument attached to an arm has exceeded a predetermined threshold the assistance module 304 may determine that the surgical robot system is in a faulty instrument state.

The assistance module 304 may be configured to detect that the surgical robot system 302 is in an energised instrument hazard state if the status data indicates that the surgical robot system is in an unsafe state to energise an energised instrument and the operator (e.g. surgeon) has attempted to energise an energised instrument. As described above, the term "energised instrument" is used herein it refer to a surgical instrument, such as, but not limited to, an electrosurgical instrument and an electrocautery instrument, that is energised with an electrical current to perform a surgical function (e.g. cutting, cauterising etc.). The assistance module 304 may be configured to detect that the surgical robot system 302 is in an unsafe state to energise an energised instrument when the assistance module 304 detects, from the status data, that: an energised instrument attached to one of the robot arms is outside the field of view of the endoscope; an energised instrument attached to one of the robot arms is not in contact with the patient's flesh; an energised instrument attached to one of the robot arms is not in a stationary position (i.e. it is currently being moved by the corresponding robot arm); an energised instrument attached to one of the robot arms is within a predetermined distance of certain parts of the patient's body (e.g. blood vessel); and/or an energised instrument attached to one of the robot arms is in contact with another instrument (which may be another energised instrument or may be a non-energised instrument).

The assistance module 304 may be configured to detect that an energised instrument attached to one of the robot arms is outside the field of view (FOV) of the endoscope by, for example, determining from information about the position and/or movement of the endoscope the field of view of the endoscope, determining from information about the position and/or movement of the arm attached to the energised instrument and/or the energised instrument the position of the energised instrument, and comparing the determined position of the energised instrument to the determined FOV of the endoscope. Alternatively, or in addition, the assistance module 304 may be configured to detect that an energised instrument is outside the FOV of the endoscope by analysing the endoscope video using video analysis techniques to determine if the energised instrument is visible in the endoscope video.

The assistance module 304 may be configured to detect that an energised instrument attached to one of the arms is not in contact with the patient's flesh or that the energised instrument is within a predetermined distance of certain parts of the patient's body by for example, analysing the endoscope video using video analysis techniques to determine if the energised instrument is in contact with the patient's flesh or that the energised instrument is within a predetermined distance of certain parts of the patient's body.

The assistance module 304 may be configured to detect that an energised instrument attached to one of the robot arms is not stationary by analysing the position and/or movement information related to the robot arms and/or instruments to determine whether the relevant arm is in motion. If the assistance module 304 determines that the relevant arm is in motion, then the assistance module 304 may determine that the energised instrument is in an unsafe condition for energising and if the operator (e.g. surgeon) attempts to energise the energised instrument while in this unsafe condition the assistance module 304 may determine that there is an energised instrument hazard. In some cases, the assistance module 304 may be configured to only determine that the energised instrument is in an unsafe condition for energising if the energised instrument is in motion and the movement or motion is not expected or is outside an acceptable range.

The assistance module 304 may be configured to detect that the surgical robot system 302 is in a potential hazard state if the assistance module detects, from the status data for the current task, one or more hazard indicators. A hazard indicator may be a condition that does not in and of itself definitively indicate there is a problem but may indicate there is a problem. Hazard indicators may include, but are not limited to; one or more the patient's vital signs and/or other health metrics falling outside a predetermined range; one or more of the operator's (e.g. surgeon's) vital signs and/or other health metrics falling outside a predetermined range; one or more of the individuals present for the task (e.g. one or more of the surgical team) speaking in a raised voice; and one or more of the individuals present for the task (e.g. one or more of the surgical team) speaking a warning word or phrase.

As described above, in some cases the status data may include patient health information or data that indicates the status of one or more of the patient's vital signs and/or one or more other health metrics. In these cases, the assistance module 304 may be configured to detect a hazard indicator when the patient health information or data indicates one or more of the patient's health metrics (e.g. vital signs) have fallen outside a predetermined range. The predetermined range may vary between health metrics (e.g. there may be a different range for respiration rate and heartrate). Similarly, in some cases the status data may include surgeon health information or data that indicates the status of one or more of the surgeon's vital signs and/or one or more other health metrics. In these cases, the assistance module 304 may be configured to detect a hazard indicator when the surgeon health information or data indicates that one or more of the surgeon's health metrics (e.g. vital signs) have fallen outside a predetermined range. In some cases, the predetermined ranges for the different medical metrics for the patient and/or surgeon may be pre-loaded into the assistance module 304 prior to starting the task. In some cases, the predetermined ranges may be learned from the status data for previously performed tasks. For example, the assistance module 304 or another computing device may identify, from the status data of previously performed tasks, the level of the different health metrics just prior to a negative outcome occurring and generate the predetermined ranges from the identified levels (e.g. a range that encompasses the lowest and highest identified levels may be selected). The predetermined ranges may be determined across all tasks, or different predetermined ranges may be determined for different tasks (i.e. different surgical procedures). For example, it may be determined from the status data for previously performed tasks that a heart rate in the range of X to Y is normal for surgery type A, but is not normal for surgery type B.

As described above, in some cases the status data may include a video and/or audio recording of the room (e.g. operating room) in which the task is performed. In these cases, the assistance module 304 may be configured to detect a hazard indicator when the assistance module 304 detects from the video and/or audio recording that an individual in the room has spoken in a raised voice. Specifically, if an individual is speaking in a raised voice it may indicate that there is some friction between individuals in the room and/or that there is an issue or problem in the room. The assistance module 304 may be able to detect a raised voice using any known speech analysis technique. Where the status data includes a video and/or audio recording, the assistance module 304 may also, or alternatively, be configured to detect a hazard indicator when the assistance module 304 detects from the video and/or audio recording that an individual in the room has spoken a warning word or phrase (i.e. a word or phrase that indicates that there may be a problem). The assistance module 304 may be configured to detect warning words and/or phrases in the video and/or audio recording using any known speech recognition or analysis technique. The list of warning words and/or phrases may be pre-loaded into the assistance module 304 prior to starting the task. In some cases, the list of warning words and/or phrases may be learned from the status data of previously performed tasks. For example, the assistance module 304 or another computing device may identify, from the status data of each of a plurality of previously performed tasks, any words or phrases spoken a predetermined period of time before a negative outcome and generate a list of identified words or phrases that are common between a predetermined number of previously performed tasks.

It will be evident to a person of skill in the art that these are example hazard indicators and there may be other conditions and/or events etc. that indicate a potential problem or issue. In some cases, the hazard indicators may be learned from the status data of previously performed tasks (e.g. surgeries). For example, in some cases, the status data related to previously performed tasks may be stored in a data repository 310 and the events or series of events preceding a negative outcome may be identified and those identified events or series of events that are common across a predetermined number of previously performed tasks may be identified as hazard indicators. For example, if the status data for a plurality of previously performed tasks indicates that steps A, B and C were performed before a negative outcome or result occurred then a hazard indicator may be identified as performance of steps A and B and step C is likely to be performed. The status data for previously performed tasks may include status data for previously performed tasks performed by the same operator (e.g. surgeon) and/or performed by other operators (e.g. surgeons). The status data for previously performed tasks may only include status data related to the same task (e.g. surgical procedure) or may include status data related to a plurality of different tasks (e.g. different surgical procedures).

The assistance module 304 may also, or alternatively, be configured to detect that the surgical robot system 302 is in a potential hazard state based on an assessment of the performance of the operator (e.g. surgeon) controlling the surgical robot system. For example, if the assistance module 304 detects that the performance of the operator (e.g. surgeon) has fallen below a predetermined threshold then the assistance module 304 may detect that the surgical robot system 302 is in a potential hazard state. In some cases, the assistance module 304 may be configured to detect that the performance of the operator (e.g. surgeon) has fallen below a predetermined threshold by comparing the status data for the current task to the status data for previously performed tasks (e.g. tasks of the same type). For example, the assistance module 304 may have access to a data repository 310 in which the status data for previously performed tasks is stored and in which the performance of the operator (e.g. surgeon) of the surgical robot system has been assessed or identified (e.g. the performance may be ranked on a predetermined scale); and the status data may be compared to the status data stored in the repository to determine the performance level of the current operator (e.g. surgeon) of the surgical robot system.

In some cases, the assistance module 304 may determine the performance level of the current operator (e.g. surgeon) operating the surgical robot system by comparing one or more performance metrics of the current operator (e.g. surgeon) to the performance metrics of the operators (e.g. surgeons) for the previously performed tasks. In some cases, the performance metrics may include one or more of: the path taken by a robot arm or instrument in performing a task or step of the task; the smoothness of the movement of the robot arm and/or instrument in performing a task or step of the task; and/or the time taken to perform the task or step of the task. Where the status data comprises information describing the position and/or movement of the arm(s) and/or instrument(s) of surgical robot system 302, the assistance module 304 may be configured to determine the path of the robot arm and/or instrument from the information describing the position and/or movement of the arm(s) and/or instrument(s). Once the path taken has been identified the assistance module 304 may be able to measure the smoothness of the path based on whether the path has smooth curves or jagged edges. As described above, in some cases the status information may comprise information explicitly identifying the task and/or step of the task that is currently being performed. In other cases, the assistance module 304 may be able to dynamically detect the current task and/or current step of the task based on other status data. In either case, the assistance module 304 may be configured to determine the time taken to perform the task or a step of the task by measuring the time between tasks or between steps of the task.

In some cases, the assistance module 304 may comprise a list of skills for which assistance can be provided and the assistance module 304 may be configured to detect that the surgical robot system is in a skill assistance state when the assistance module detects, from the status data that one of the skills in the list of skills is about to be performed by the surgical robot system or that the surgical robot system has started to perform one of the skills in the list of skills. For example, the list of skills for which assistance may be provided may include, but are not limited to, performing a suture, or performing a knot. In these cases, the assistance module 304 may be configured to detect that the operator (e.g. surgeon) is about to use the surgical robot system to perform a suture if a suturing instrument has been attached to one of the robot arms. It will be evident to a person of skill in the art that these are examples only of skills for which assistance can be provided and that there may be other skills for which assistance can be provided.

In some cases, the assistance module 304 may comprise a list of tasks or steps of a task for which procedural assistance can be provided and the assistance module 304 can be configured to detect that the surgical robot system is in a procedural assistance state when the assistance module 304 detects, from the status data, that one of the tasks or steps of a task for which procedural assistance can be provided is about to be executed or the operator (e.g. surgeon) has started to perform one of the tasks or steps of a task on the list. As described above, in some cases the status data may comprise information that explicitly identifies the task or step that is currently being performed. In other cases, the assistance module 304 may be able to dynamically determine the task or step of a task that is currently being performed from other status data.

If the assistance module 304 determines that the surgical robot system is not in an assistance state, then the method returns to block 502 where the assistance module 304 receives the next set of status data and determines from the next set of status data whether the surgical robot system is in an assistance state. If, however, the assistance module 304 determines that the surgical robot system is in an assistance state then the method 500 proceeds to block 506.

At block 506, in response to determining that the surgical robot system is in an assistance state, the assistance module 304 is configured to cause the surgical robot system to provide assistance to one or more users in performing the task. The assistance module 304 may cause the surgical robot system to provide assistance to one or more users in performing the task by (i) controlling all or portion of the movement of one or more of the robot arms and/or (ii) causing the surgical robot system to output assistance information to one or more users that can assist one or more users in performing the task.

The assistance module 304 may be configured to control the movement of one or more robot arms, by transmitting control signals to, for example a control unit 420, which causes the control unit 420 to control the operation of the motors 416 of one or more arms to cause the one or more arms 402 to operate in a particular manner. In some cases, the assistance module 304 may be configured to control the movement of one or more robot arms to either (i) inhibit or restrict the movement of the robot arm(s); or (ii) cause the robot arm(s) to move in a predetermined manner. Inhibiting or restricting the movement of a robot arm may comprise preventing the robot arm from moving in one or more degrees of freedom and/or directions, and/or constraining the movement of the robot arm in one or more degrees of freedom and/or directions (e.g. restricting the movement of the robot arm to movement in a predetermine manifold). The assistance module 304 may be configured to inhibit or restrict the movement of one or more robot arms to, for example, prevent a hazard from occurring or to restrict the use of an instrument or robot arm in unsafe conditions. Causing a robot arm to move in a predetermined matter may comprise, for example, causing the robot arm to follow a predetermined path. The assistance module 304 may be configured to cause one or more robot arms to move in a predetermined manner to, for example. (i) perform motion smoothing; (ii) perform an automated surgical action (e.g. perform a knot); (iii) perform an automated non-surgical action (e.g. perform an instrument change).

The assistance module 304 may be configured to cause the surgical robot system to output assistance information by transmitting one or more control signals to, for example, the control unit 420, which causes the control unit 420 to output assistance information to one or more users of the surgical robot system 302. The assistance information may be output to the user in any suitable form such as, but not limited to, audibly and/or visually. For example, where the surgical robot system comprises a speaker or other audio output device the assistance module 304 may be configured to send control signals to the control unit 420 which cause the control unit 420 to audibly output via the speaker or other audio output device assistance information. Where the surgical robot system 302 comprises one or more devices, such as a display, that are capable of conveying information visually to a user the assistance module 304 may be configured to send control signals to the control unit 420 which cause the control unit 420 to visually output, via the display or other visual output device(s) assistance information. In some cases the surgical robot system 302 may comprise lights on the robot arms which can be used to convey information to users of the surgical robot system. In these cases, all or a portion of the assistance information may be conveyed or presented to the user(s) via the lights on the robot arms.

The assistance information may comprise any information that can assist the user(s) in performing the task. Examples of assistance information include but are not limited to: a list of steps to execute to complete a task or a step of a task; an indication that an instrument change is proposed; a proposed port placement; and an alert that a potential hazard state has been detected.

In some cases, prior to causing the surgical robot system 302 to provide assistance to one or more users of the surgical robot system in performing the task, the assistance module 304 may be configured to request input from the user(s) as to whether they wish assistance to be provided. In these cases, the assistance module 302 may be configured to only cause the surgical robot system 302 to provide assistance to a user of the surgical robot system in response to receiving input indicating that assistance is to be provided. Whether or not the surgical robot system 302 requests input from the user prior to providing assistance may depend on the type of assistance that is being provided and/or the assistance state that is detected by the assistance module 304 in block 504. For example, the assistance module 302 may be configured to request input from the user prior to controlling all or a portion of the movement of a robot arm, but not request input from the user prior to providing assistance information.

The type of assistance that is provided may be based on the assistance state that is detected by the assistance module 304 in block 504. For example, for some types of assistance states the assistance module 304 may only be capable of providing one type of assistance (e.g. outputting assistance information) whereas for other types of assistance states the assistance module may be able to provide multiple types of assistance (e.g. outputting assistance information and controlling the movement of one or more robot arms).

When the assistance module 304 has determined (at block 504) that the surgical robot system 302 is in a collision state the assistance module 304 may be configured to cause the surgical robot system to output assistance information that notifies one or more users of the surgical robot system that a collision (or a predicted collision) has been detected and optionally, provides information about the collision (or predicted collision) such as, but not limited to, the type of collision (e.g. whether the collision was between arms, instruments or between an arm and an instrument) and the elements (e.g. robot arms and/or instruments) involved in the collision. For example, where the robot arms comprise controllable lights (e.g. a set of controllable light emitting diodes (LEDs)), the assistance module 302 may be configured to cause the lights of the relevant robot arm to turn a predetermined colour (e.g. to red, for example) or to emit light in a predetermined pattern to indicate the robot arms that were involved in the collision.

Alternatively, or, in addition, the assistance module 304 may be configured to inhibit the movement of the relevant robot arms (the robot arms involved in the collision or predicted collision) so as to prevent a predicted collision or to stop the collided components from being damaged by further movement towards each other. For example, the assistance module 304 may be configured to prevent the relevant arms (the arms involved in the collision or predicted collision) from moving at all until they are manually moved apart. In other examples, the assistance module may be configured to prevent the relevant robot arms from moving towards one another but allow the relevant robot arms to move in other directions (e.g. away from one another). In some cases, where a collision has already occurred, once the assistance module 304 has prevented the movement of the relevant arms (entirely or towards one another) for a pre-determined period of time the assistance module 304 may be configured to automatically cause the relevant arms to move apart (e.g. in the opposite direction of the collision). In some cases, the assistance module 304 may first request input from a user of the surgical robot system before moving the relevant arms apart and only move the relevant arms apart once a user has confirmed that the relevant arms are to be moved apart.

When the assistance module 304 has determined (at block 504) that the surgical robot system 302 is in a faulty instrument state or an incorrect instrument state the assistance module 304 may be configured to cause the surgical robot system to output assistance information that notifies one or more users of the surgical robot system that a faulty instrument and/or incorrect instrument has been detected. The assistance module 302 may also be configured to cause the surgical robot system to: output information about the faulty or incorrect instrument such as, but not limited to, which instrument is faulty and/or the arm to which the faulty instrument is currently attached; and/or output information that advises one or more users of the surgical robot system that an instrument change is recommended. For example, where the robot arms comprise controllable lights, the assistance module may be configured to indicate the robot arm that has the faulty instrument, or the incorrect instrument, attached thereto by causing the lights of the relevant arm to turn a specific colour (e.g. orange) or to emit light in a particular pattern.

Alternatively, or in addition, the assistance module 304 may be configured to automatically perform an instrument change (i.e. to automatically change the faulty or incorrected instrument). When the assistance module 304 has determined (at block 504) that the surgical robot system is in a faulty instrument state 304 then the automatic instrument change replaces the faulty instrument with an instrument of the same type. In contrast, when the assistance module 304 has determined (at block 504) that the surgical robot system is in an incorrect instrument state then the automatic instrument change replaces the incorrect instrument with an instrument of a type suitable for performing the current task or step of the task.

To be able to perform an automated instrument change the surgical robot system may comprise: an instrument rack in which instruments that can be attached to a robot arm of the surgical robot system are situated; and a loading robot arm that is capable of (i) removing or detaching an instrument from a selected robot arm; (ii) retrieving a particular instrument from the instrument rack; and (iii) attaching the particular instrument to a selected robot arm. In some cases, the assistance module 304 may first request input from a user of the surgical robot system (via, for example the command interface 426) on whether an automated instrument change is to be performed, and only if a user confirms that an automated instrument change is to be performed does the assistance module 304 cause an automated instrument change to be performed. Where the assistance module 304 has determined (at block 504) that the surgical robot system is in an incorrect instrument state and there is a plurality of suitable instrument types the assistance module 304 may be configured to request input from a user of the surgical robot system on which of the plurality of suitable instruments are to be used.

When the assistance module 304 has determined (at block 504) that the surgical robot system 302 is in an energised instrument hazard state the assistance module 304 may be configured to cause the surgical robot system to prevent energisation of the relevant energised instrument. The assistance module 304 may be configured to cause the surgical robot system to prevent energisation of the relevant energised instrument by sending a control signal to the control unit 420 which causes the control unit 420 to prevent an energising electrical current from being sent to the relevant energised instrument. The assistance module 304 may also be configured to cause the surgical robot system 302 to output information notifying one or more users of the surgical robot system that an energised instrument hazard state has been detected and/or that the relevant energised instrument cannot be energised. In some cases, the assistance module 304 may also be configured to ask for user input (e.g. via the command interface) on whether the energisation prevention should be overridden. If a user provides input that the energisation prevention should be overridden, then the assistance module 304 may be configured to cause the surgical robot system to allow energisation of the relevant energised instrument.

When the assistance module 304 has determined (at block 504) that the surgical robot system 302 is in a potential hazard state the assistance module 304 may be configured to cause the surgical robot system 302 to output information that notifies one or more users of the surgical robot system that a potential hazard state has been detected. The assistance module 302 may also be configured to cause the surgical robot system to output information about which hazard indicators were detected (e.g. whether the vital signs or other health metrics of the patient or surgeon indicate there is a problem or whether the level of speech or the actual words spoken by the individual or team in the room indicates there may be a problem). The assistance module 304 may also be configured to request input from a user of the surgical robot system (via, for example, the command interface) as to whether the task should be paused. If a user provides input that indicates that the task should be paused the assistance module 304 may be configured to cause the movement of one or more of the robot arms to be inhibited.

When the assistance module 304 has determined (at block 504) that the surgical robot system is in a skill assistance state the assistance module 304 may be configured to cause the surgical robot system 302 to output information that notifies one or more users of the surgical robot system that a skill assistance state has been detected. The assistance module 304 may also, or alternatively be configured to control one or more robot arms of the surgical robot system 302 to perform all or a portion the skill and/or inhibit movement of one or more surgical robot arms so as to aid the operator (e.g. surgeon) in performing the skill. For example, as described above, the assistance module 304 may be configured with an ideal or preferred path for a robot arm/instrument attached thereto to take to perform a knot and may be able to control the robot arms to follow the ideal or preferred path to perform the knot when the assistance module 304 has determined that a knot is about to be performed using the surgical robot system. In some cases, the assistance module 304 may be configured to request input from a user (via, for example, the command interface) as to whether the skill should be automatically performed and only if a user indicates that the skill should be automatically performed does the assistance module 304 control the robot arm(s) to automatically perform the skill.

In some cases, alternatively to controlling the robot arm to perform all or a portion of the skill, the assistance module 304 may be configured to inhibit movement of one or more surgical robot arms so as to aid the operator (e.g. surgeon) in performing the skill. For example, as described above, the assistance module may be configured with an ideal or preferred path for a robot arm/instrument attached thereto to take to perform a knot and the assistance module 304 may restrict movement of the relevant robot arm to within a predetermined distance of the ideal path. This would allow the surgeon to control the movement of the relevant robot arm/instrument within the predetermined distance of the ideal path and to control the rate at which the relevant robot arm/instrument follows the path.

In some cases, the path of a good knot may have been learned from the status data for previously performed tasks that involved performing a knot. For example, the assistance module 304 or another computing device may receive the status data related to a plurality of tasks which involved performing a knot in which an assessment of the quality of the knot is provided (e.g. the knots may have been rated on a scale) and identify a path that is common or links the paths of the best knots. The path that is common or links the paths of the best knots may be a path that has a maximum mean square distance from the path of the knots at or above a particular ranking.

When the assistance module 304 has determined (at block 504) that the surgical robot system is in a procedure assistance state the assistance module may be configured to cause the surgical robot system to output information that provides guidance on how to perform the task, or step of the task. The information that provides guidance on how to perform the task may comprise one or more of: information indicating what step or steps are to be performed next; information indicating which instrument should be selected next; information indicating which hand controller each active arm should be associated with; information indicating a path the active robot arm should follow to perform the task in an efficient manner (e.g. a recommended path the active robot arm/instrument is to follow may be displayed on a display screen).

In some cases, the guidance on how to perform the task, or step of the task is determined from the status data related to previously performed tasks. For example the assistance module 304, or another computing-based device, may be configured to identify preferred steps of the procedure, preferred instruments, preferred hand controllers and/or preferred paths taken by an instrument by comparing status data for previously performed tasks to identify patterns therein. For example, where the status data includes or is augmented with outcome information indicating the outcome of the task (e.g. outcome of the patient), the assistance module 304, or another computing-based device may be configured to identify the steps of a particular task, the instruments, hand controllers and/or paths taken by the instruments which produced the best outcomes from the status data of previously performed tasks. The status data that is analysed may include status data for similar tasks (e.g. for the same or similar surgical procedure); status data for tasks performed by similar operators (e.g. surgeons); and/or status data for patients similar to the current patent. It will be evident to a person of skill in the art that these are examples of guidance information and examples of how that guidance information may be obtained and that other guidance information may be provided, and the guidance information may be generated in another manner. For example, in other cases the guidance information may be preconfigured or predetermined.

In some cases, the level of assistance that is provided to the user(s) may be based on the skill level of the operator (e.g. surgeon) controlling the surgical robot system. For example, more assistance (e.g. more assistance information) may be provided to an operator (e.g. surgeon) with a lower skill level and less assistance (e.g. less assistance information) may be provided to an operator (e.g. surgeon) with a higher skill level. For example, an operator (e.g. surgeon) with a lower skill level may be provided with detailed instructions on how to perform a skill or a particular step of the task, whereas an operator (e.g. surgeon) with a higher skill level may only be provided with the odd hint or tip. In some cases, the skill level of the operator (e.g. surgeon) may be explicitly provided to the assistance module 304 as part of the status data, or in another manner (e.g. as part of the set-up for the task). In other cases, the skill level of the operator (e.g. surgeon) controlling the surgical robot system may be dynamically determined from the status data for the current task (e.g. surgical procedure) or from the status data for previous tasks performed by the operator (e.g. surgeon).

As described above, the performance of the operator (e.g. surgeon) controlling the surgical robot system may by assessed or determined by comparing one or more performance metrics of the current operator (e.g. surgeon) to the performance metrics of other operators (e.g. surgeons) for the previously performed tasks. In some cases, the performance metrics may include one or more of: the path taken by a robot arm or instrument in performing a task or step of the task; the smoothness of the movement of the robot arm and/or instrument in performing a task or step of the task; and/or the time taken to perform the task or step of the task. Where the status data comprises information describing the position and/or movement of the arm(s) and/or instrument(s) of the surgical robot system 302, the assistance module 304 may be configured to determine the path of the robot arm and/or instrument from the information describing the position and/or movement of the arm(s) and/or instrument(s). Once the path taken has been identified the assistance module 304 may be able to measure the smoothness of the path based on whether the path has smooth curves or jagged edges. The status data may comprise information explicitly identifying the current task or the current step of the task or the assistance module 304 may dynamically detect the current task and/or current step of the task based on other status data. In either case, the assistance module 304 may be configured to determine the time taken to perform the task or a step of the task by measuring the time between tasks or between steps of the task.

In some cases, in addition to providing assistance to one or more users of a surgical robot system in response to detecting that the surgical robot system is in an assistance state, the assistance module 304 may also be configured to provide other feedback information to the user(s) of the surgical robot system or to another party during the task (e.g. surgery) or after the task (e.g. surgery). For example, the assistance module 304 may be configured to provide feedback on the operator's performance during the task that indicates how the operator (e.g. surgeon) is performing relative to their previous performances of the same task, and/or relative other operators (e.g. surgeons) who have performed the same task (e.g. surgical procedure). For example, the assistance module 304 may be configured to measure one or more operator performance metrics such as, but not limited to smoothness, path taken, and time taken to perform a task or a step of a task etc. The measured performance metrics may then be compared to the operator's previous performance of the task or other operator's previous performances of the task to provide feedback on the operator's performance. For example, the assistance module 304 may be configured to provide feedback to the operator such as, but not limited to: "you are going faster than you normally do", or "you are going slower than your colleagues".

In another example, the assistance module 304 may also, or alternatively, be configured to measure metrics that relate to other users of the surgical robot system (e.g. other members of the surgical team) and generate feedback information related thereto. For example, the assistance module 304 may be configured to measure how many instruments are used during the task, the number of instrument changes, how long it takes to do each instrument change, how long it takes to prepare (e.g. drape) the surgical robot system for the task (e.g. surgery). The assistance module 304 may be configured to cause the surgical robot system to output the measured metrics or may provide the measured metrics to another party.

In yet another example, the assistance module 304 may also, or alternatively, be configured to measure metrics about the surgical robot system and generate feedback information related thereto. For example, the assistance module 304 may be configured to detect from the status data when an instrument change has occurred and if the assistance module 304 has detected that a first instrument attached to an arm is replaced with a second instrument of the same type within a predetermined period of time of the first instrument being attached to the arm the assistance module 304 may be configured to automatically detect that the first instrument was faulty. This information may be recorded and reported to another party so that a new instrument of that type can be ordered, for example.

In yet another example, the assistance module 304, or another computing based device, may also, or alternatively, be configured to analyse the status data to generate feedback information for use in a process or procedure performed before or after the task or a similar task. In particular, the assistance module 304 may be configured to analysis the status data to identify information that can be used in scheduling future tasks or other procedures. For example, the assistance module 304 may be configured to predict from the status data when the task will be complete and if the predicted completion time is below a predetermined threshold (e.g. 1 hour) notify another party (e.g. the operating room manager) so that the next task in that operating room can be scheduled and the next patient can be prepared and/or so that the operator of the surgical robot system (e.g. surgeon) can be scheduled for another task. In another example, the assistance module 304 may be configured to, after the task is complete, compare the status data (including the outcomes) to the status data for similar procedures performed by the same operator (e.g. surgeon) to determine the best time (e.g. time of the day and/or day of the week) for that operator to perform that particular task and output feedback information indicating the determined best time for that operator to perform that particular task.

It will be evident to a person of skill in the art that these are examples of additional feedback information that may be generated and provided by the assistance module 304 and that any information that can be obtained from the status data and/or a comparison of the status data to the status data for previously performed tasks (e.g. surgeries) can be used to generate additional feedback information.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein. In view of the foregoing description it will be evident to a person skilled in the art that various modifications may be made within the scope of the invention.

What is claimed is:

1. A system for providing assistance to a user of a surgical robot system, the system comprising:
    a surgical robot system comprising at least one surgical robot having a base, and an arm extending from the base to an attachment for an instrument, the arm comprising a plurality of joints whereby the configuration of the arm can be altered; and
    an assistance module configured to:
        receive, while the surgical robot system is being used to perform a task, status data comprising a video and/or audio recording of a room in which the task is performed;
        determine that the surgical robot system is in a potential hazard state when one or more hazard indicators are detected from the status data, the one or more hazard indicators comprising one or more individuals present for the task speaking a warning word or phrase, wherein the warning word or phrase is learned from status data of previously performed tasks; and
        in response to determining that the surgical robot system is in a potential hazard state, cause the surgical robot system to provide potential hazard assistance to the user while the surgical robot system is being used to perform the task,
    wherein the assistance module is configured to identify, from the status data of each of a plurality of previously performed tasks, any word or phrase spoken within a predetermined period of time before a negative output and make any identified word or phrase that is common between a predetermined number of previously performed tasks a warning word or phrase.

2. The system of claim 1, wherein causing the surgical robot system to provide potential hazard assistance comprises outputting information about the one or more detected hazard indicators.

3. The system of claim 2, wherein, when the one or more detected hazard indicators comprises one or more individuals present for the task speaking a warning word or phrase, outputting information about the one or more detected hazard indicators comprises identifying the warning word or phrase.

4. The system of claim 1, wherein causing the surgical robot system to provide potential hazard assistance comprises requesting input from a user of the surgical robot system as to whether the task should be paused.

5. The system of claim 4, wherein causing the surgical robot system to provide potential hazard assistance further comprises, in response to a user of the surgical robot system providing input that the task should be paused, cause movement of one or more of the at least one arm to be inhibited.

6. The system of claim 1, wherein the status data comprises data indicating a status of one or more health metrics of an operator of the surgical robot system.

7. The system of claim 6, wherein the one or more hazard indicators comprises one or more health metrics of the operator of the surgical robot system falling outside a predetermined range.

8. The system of claim 6, wherein each of the one or more health metrics of the operator of the surgical robot system is associated with a predetermined range, and each predetermined range has been learned from status data for previously performed tasks.

9. The system of claim 1, wherein the one or more hazard indicators comprises events or patterns in the status data of previously performed tasks that preceded a hazard.

10. The system of claim 1, wherein the assistance module is configured to determine that the surgical robot system is in a potential hazard state when the assistance module determines, from the status data, that a performance of an operator of the surgical robot system has fallen below a predetermined threshold.

11. The system of claim 10, wherein the assistance module is configured to determine that the performance of the operator of the surgical robot system has fallen below a predetermined threshold by comparing the status data to status data for previously performed tasks.

12. The system of claim 10, wherein the assistance module is configured to determine, from the status data, that a performance of the operator of the surgical robot system has fallen below a predetermined threshold by determining, from the status data, one or more performance metrics of the operator of the surgical robot system, the one or more performance metrics comprising one or more of: a path taken by a robot arm or instrument in performing the task or a step of the task, a smoothness of movement of a robot arm in performing the task or a step of the task, and a time taken to perform the task or a step of the task.

* * * * *